United States Patent
Bi et al.

(10) Patent No.: US 10,145,926 B2
(45) Date of Patent: Dec. 4, 2018

(54) PHASE-CYCLED STEADY-STATE FREE PRECESSION IMAGING

(71) Applicant: Siemens Healthcare GmbH, Erlangen (DE)

(72) Inventors: Xiaoming Bi, Oak Park, CA (US); Yutaka Natsuaki, Riverside, CA (US); Kevin Johnson, Tuscon, AZ (US); Gerhard Laub, San Mateo, CA (US)

(73) Assignee: Siemens Healthcare GmbH, Erlangen (DE)

( * ) Notice: Subject to any disclaimer, the term of this patent is extended or adjusted under 35 U.S.C. 154(b) by 363 days.

(21) Appl. No.: 14/953,619

(22) Filed: Nov. 30, 2015

(65) Prior Publication Data

US 2017/0153310 A1 Jun. 1, 2017

(51) Int. Cl.
*G01V 3/00* (2006.01)
*G01R 33/565* (2006.01)
(Continued)

(52) U.S. Cl.
CPC ........ *G01R 33/56509* (2013.01); *A61B 5/055* (2013.01); *A61B 5/7207* (2013.01);
(Continued)

(58) Field of Classification Search
CPC .. G01R 33/34; G01R 33/34007; G01R 33/36; G01R 33/3635; G01R 33/3642;
(Continued)

(56) References Cited

U.S. PATENT DOCUMENTS

| 7,020,509 B2 | 3/2006 | Heid |
| 8,452,065 B2 | 5/2013 | Azar et al. |

(Continued)

FOREIGN PATENT DOCUMENTS

WO 2014085288 A1 6/2014

OTHER PUBLICATIONS

Fuchs, Friedrich et al., "TrueFISP—technical considerations and cardiovascular applications", European Journal of Radiology, 46 (2003), DOI: 10.1016/S0720-048X(02)00330-3, (pp. 28-32, 5 total pages).

(Continued)

Primary Examiner — Thang Le

(57) ABSTRACT

A system includes applying, to patient tissue, a first imaging sequence comprising first balanced gradient pulse trains and RF pulses, where phases of successive RF pulses in the first imaging sequence differ by a first pulse phase increment, detecting first signals emitted from the patient tissue in response to the first imaging sequence, and to generate a first image based on the first signals, applying, to the patient tissue, a second imaging sequence comprising second balanced gradient pulse trains and RF pulses, where phases of successive RF pulses in the second imaging sequence differ by a second pulse phase increment different from the first pulse phase increment, detecting second signals emitted from the patient tissue in response to the second imaging sequence, and to generate a second image based on the second signals, applying motion-correction processing to the first image to generate a first motion-corrected image, applying motion-correction processing to the second image to generate a second motion-corrected image, and generating a composite image based on the first motion-corrected image and the second motion-corrected image.

12 Claims, 7 Drawing Sheets

(51) Int. Cl.
*G01R 33/385* (2006.01)
*G01R 33/36* (2006.01)
*G01R 33/54* (2006.01)
*A61B 5/055* (2006.01)
*A61B 5/00* (2006.01)

(52) U.S. Cl.
CPC ....... *G01R 33/3614* (2013.01); *G01R 33/385* (2013.01); *G01R 33/543* (2013.01); *G01R 33/546* (2013.01); *A61B 2576/00* (2013.01)

(58) Field of Classification Search
CPC .. G01R 33/48; G01R 33/4818; G01R 33/481; G01R 33/4824; G01R 33/446; G01R 33/4835; G01R 33/4828; G01R 33/54; G01R 33/543; G01R 33/561; G01R 33/563; G01R 33/565; G01R 33/5611; G01R 33/5612; G01R 33/583; G01R 33/5659; G01R 33/56518; G01R 33/56536; G01R 33/56572; G01R 33/5614; G01R 33/5616; G01R 33/56509; G01R 33/341; G01R 33/385; G01R 33/56358; A61B 5/055; A61B 5/0555; A61B 5/7278; A61B 5/725
See application file for complete search history.

(56) References Cited

U.S. PATENT DOCUMENTS

| | | | |
|---|---|---|---|
| 8,744,551 B2 | 6/2014 | Koktzoglou et al. | |
| 2003/0102864 A1* | 6/2003 | Welch | G01R 33/56509 324/307 |
| 2009/0253979 A1* | 10/2009 | Ehman | A61B 5/416 600/410 |
| 2010/0232667 A1 | 9/2010 | Azar et al. | |
| 2012/0302871 A1* | 11/2012 | Yamada | A61B 5/055 600/413 |
| 2015/0369891 A1* | 12/2015 | Miyazaki | G01R 33/5617 324/309 |
| 2017/0227621 A1* | 8/2017 | Hirai | G01R 33/5659 |
| 2017/0281041 A1* | 10/2017 | Yokosawa | A61B 5/055 |

OTHER PUBLICATIONS

Gill, Ritu R. et al., "Diffusion-Weighted MRI of Malignant Pleural Mesothelioma: Preliminary Assessment of Apparent Diffusion Coefficient in Histologic Subtypes", Cardiopulmonary Imaging Original Research, Aug. 2010, DOI:10.2214/AJR.09.3519, downloaded from www.ajronline.org on Jul. 8, 2015. (pp. 125-130, 6 total pages).

Winkelmann, Stefanie et al., "An Optimal Radial Profile Order Based on the Golden Ratio for Time-Resolved MRI", IEEE Transactions on Medical Imaging, vol. 26, No. 1, Jan. 2007, DOI:10.1109/TMI.2006.885337, (pp. 68-76, 9 total pages).

Block, Kai Tobias et al., "Towards Routine Clinical Use of Radial Stack-of-Stars 3D Gradient-Echo Sequences for Reducing Motion Sensitivity", Journal of the Korean Society of Magnetic Resonance in Medicine, 18(2), 2014, pISSN:1226-9751 / eISSN 2288-3800, http://dx.doi.org/10.13104/jksmrm.2014 18.2.87, (pp. 87-106, 20 total pages.

Zhang, Tao et al., "Fast Pediatric 3D Free-Breathing Abdominal Dynamic Contrast Enhanced MRI With High Spatiotemporal Resolution", Journal of Magnetic Resonance Imaging, 41, (2015), DOI:10.1002/jmri.24551, (pp. 460-473, 14 total pages).

Rosenkrantz, Andrew B. et al., "Dynamic Contrast-Enhanced MRI of the Prostate With High Spatiotemporal Resolution Using compressed Sensing, Parallel Imaging, and Continuous Golden-Angle Radial Sampling: Preliminary Experience", Journal of Magnetic Resonance Imaging, 41, (2015), DOI:10.1002/jmri.24661, (pp. 1365-1373, 9 total pages).

Song, Hee Kwon et al., "Dynamic MRI With Projection Reconstruction and KWIC Processing for Simultaneous High Spatial and Temporal Resolution", Magnetic Resonance in Medicine, 52, (2004), DOI:10.1002/mrm.20237, (pp. 815-824, 10 total pages).

Song, Hee Kwon et al., "Noncontrast Enhanced Four-Dimensional Dynamic MRA with Golden Angel Radial Acquisition and K-space Weighted Image Contr4ast (KWIC) Reconstruction", Magnetic Resonance in Medicine 00, (2013), DOI:10.1002/mrm.25057, (pp. 1-11, 11 total pages).

Chandarana, Hersh et al., "Free-Breathing Contrast-Enhanced Multiphase MRI of the Liver Using a Combination of Compressed Sensing, Parallel Imaging, and Golden-Angle Radial Sampling", NIH Public Access Author Manuscript, Invest Radial., Jan. 2013, 48(1), DOI:10.1097/RLI.0b013e318271869c, 17pgs.

Kawaji, Keigo et al., "Whole Heart Coronary Imaging with Flexible Acquisition Window and Trigger Delay", Plos One, Feb. 26, 2015, DOI:10.1371/journal.pone.0112020, (1-14, 14 total pages).

Herborn, Christoph et al., "Evaluation of Steady state free precession imaging of the pancreas", Eur Radiol, 15, (2005), DOI:10.1007/s00330-005-2774-1, (pp. 1629-1633, 5 total pages ).

Carr, H. Y. "Steady-State Free Precession in Nuclear Magnetic Resonance", Physical Review, vol. 112, No. 5, Dec. 1, 1958, (pp. 1693-1708, 16 total pages).

Herborn, Christoph U. et al., MRI of the Liver: Can True FISP Replace HASTE?, Journal of Magnetic Resonance Imaging, 17, (2003), DOI:10.1002/jmri.10248, (pp. 190-196, 7 total pages).

Numminen, Kirsti et al., "Magnetic Resonance Imaging of the Liver: True Fast Imaging with Steady State Free Precession Sequence Facilitates Rapid and Reliable Distinction Between Hepatic Hemangiomas and Liver Malignancies", Journal of Computer Assisted Tomography, vol. 27, No. 4, 2003, (pp. 571-576, 6 total pages).

Xie, Jingsi et al., "3D Flow-Independent Peripheral Vessel Wall Imaging Using T2-Prepared Phase-Sensitive Inversion-Recovery Steady-State Free Precession", Journal of Magnetic Resonance Imaging, 32, (2010), DOI:10.1002/jmri.22272, (pp. 399-408, 10 total pages).

Vasanawala, Shreyas S. et al., "Linear Combination Steady-State Free Precession MRI", Magnetic Resonance in Medicine, 43, (2000), (pp. 82-90, 9 total pages).

Bangerter, Neal K. et al., "Analysis of Multiple-Acquisition SSFP", Magnetic Resonance in Medicine, 51, (2004), DOI:10.1002/mrm.20052, (pp. 1038-1047, 10 total pages).

Xue, Hui et al., "Phase-Sensitive Inversion Recovery for Myocardial T1 Mapping with Motion Correction and Parametric Fitting", Magn Reson Med. Author Manuscript, May 2013, vol. 69, No. 5, DOI:10.1002/mrm.24385, (pp. 1408-1420, 24 total pages).

Kellman, Peter et al., "High Spatial and Temporal Resolution Cardiac Cine MRI from Retrospective Reconstruction of Data Acquired in Real Time Using Motion Correction and Resorting", Magnetic Resonance in Medicine, 62, (2009), DOI:10.1002/mrm.22153, (pp. 1557-1564, 8 total pages).

Stanisz, Greg J. et al., "T1, T2 Relaxation and Magnetization Transfer in Tissue at 3T", Magnetic Resonance in Medicine, 54, (2005), DOI:10.1002/mrm.20605, (pp. 507-512, 6 total pages).

Feng, Li, et al. "Golden-angle radial sparse parallel MRI: combination of compressed sensing, parallel imaging, and golden-angle radial sampling for fast and flexible dynamic volumetric MRI." Magnetic resonance in medicine 72.3 (2014): 707-717.

* cited by examiner

PHASE-CYCLED STEADY-STATE FREE PRECESSION IMAGING

BACKGROUND

Magnetic resonance (MR) imaging uses the nuclear magnetic resonance phenomenon to produce images of internal patient volumes. MR imaging generally involves subjecting tissue to a uniform main magnetic field. This causes the individual magnetic moments of the nuclear spins in the tissue to process about the magnetic field at their characteristic Larmor frequency as they attempt to align with the field, and produces a net magnetic moment $M_z$ in the direction of the main magnetic field. The tissue is then subjected to a radiofrequency (RF) field near the Larmor frequency, which may rotate, or "tip", the net magnetic moment $M_z$ into the x-y plane at a corresponding flip angle to produce a net transverse magnetic moment $M_t$ which is rotating, or spinning, in the x-y plane at the Larmor frequency. Next, the RF field is terminated, causing the excited spins to emit signals as they return to their prior state.

Magnetic field gradients $G_x$, $G_y$, and $G_z$ are used to distort the main magnetic field in a predictable way so that the Larmor frequency of nuclei within the main magnetic field varies as a function of position. Accordingly, an RF field which is near a particular Larmor frequency will tip the net aligned moment $M_z$ of those nuclei located at positions in the distorted magnetic field which correspond to the particular Larmor frequency, and signals will be emitted only by those nuclei after the RF field is terminated. The emitted signals are detected, digitized and processed to reconstruct an image using one of many well-known MR reconstruction techniques.

An MR sequence describes a set of timings and characteristics of the above-described fields, gradients and pulses, which may be used to acquire an MR image. Known steady-state free precession MR sequences maintain a steady-state of longitudinal magnetization and transverse magnetization by applying balanced magnetic field gradients between successive equidistant RF pulses. The term "balanced" refers to zero net gradient-induced phasing over a $T_R$ (i.e., repetition time) interval between RF pulses.

Short $T_R$ intervals are desired because, if the $T_R$ interval is too long, the spins will pick up an increasing amount of phase errors from one $T_R$ interval to the next due to off-resonance effects. MR imaging systems are currently capable of applying appropriate balanced magnetic field gradients within short $T_R$ intervals, but typically at field strengths of 1.5 T and lower. At higher field strengths, increasing off-resonance effects require ever-decreasing $T_R$ intervals. Even if an MR imaging system could successfully generate and apply balanced magnetic field gradients during these shorter $T_R$ intervals, the shorter $T_R$ intervals reduce the upper limit of the flip angle. The combination of shorter $T_R$ interval and lower flip angle leads to decreased T2 weighting, which is undesirable for many types of MR imaging.

DETAILED DESCRIPTION

The following description is provided to enable any person in the art to make and use the described embodiments. Various modifications, however, will remain readily apparent to those in the art.

Some embodiments provide a technical solution to the technical problem of poor MR image quality resulting from the technical considerations described above. Some embodiments provide improved image quality at higher field strengths and allow for longer $T_R$ intervals. Some embodiments therefore also support the use of larger flip angles at higher field strengths with longer $T_R$ intervals.

Figure 1:
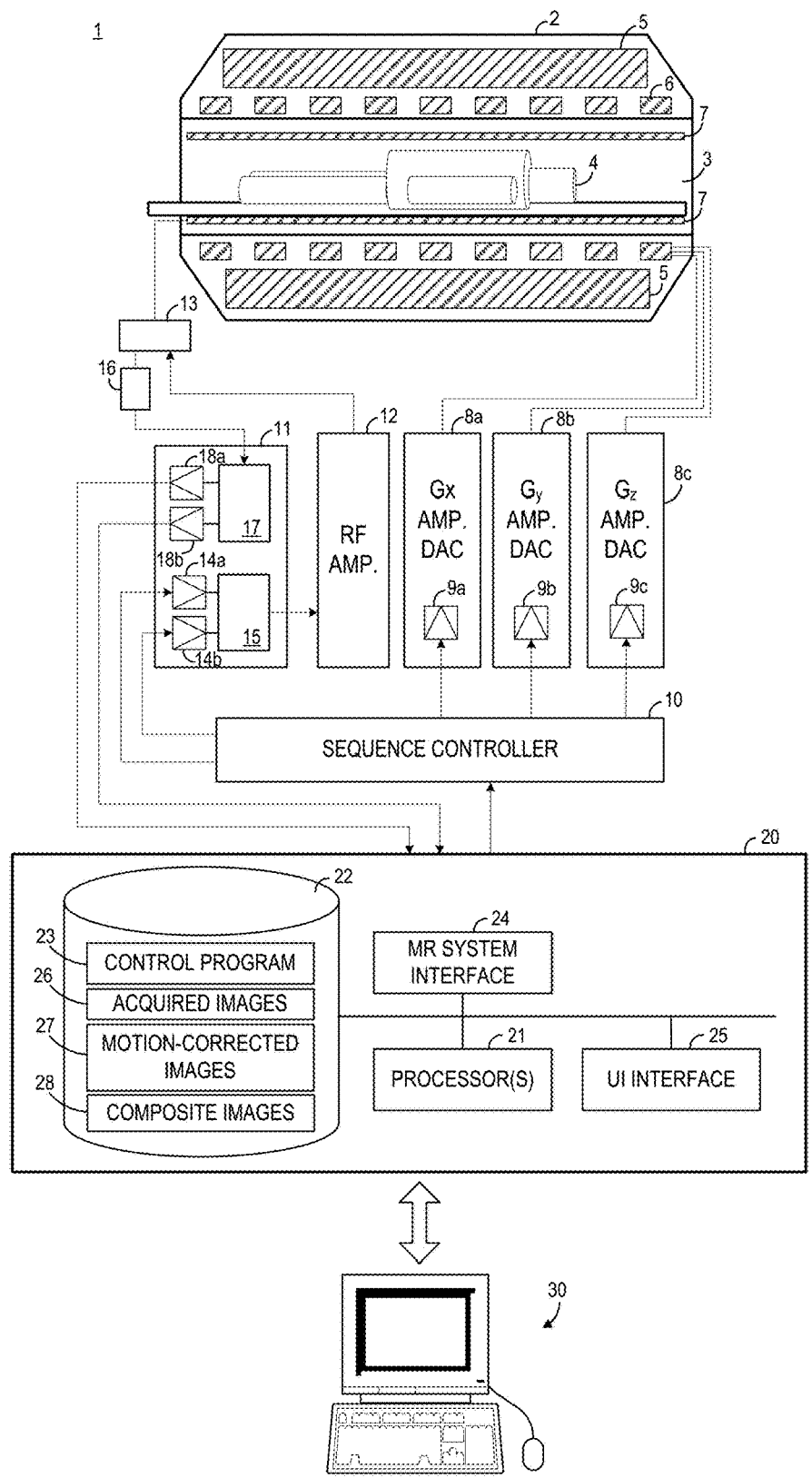
FIG. 1 is a block diagram of an MR imaging system according to some embodiments.

FIG. 1 illustrates MR imaging system 1 according to some embodiments. MR imaging system 1 includes MR imaging chassis 2, which defines bore 3 in which patient 4 is disposed. MR imaging chassis 2 includes polarizing main magnet 5, gradient coils 6 and RF coil 7 arranged about bore 3. According to some embodiments, polarizing main magnet 5 generates the uniform main magnetic field mentioned above (i.e., field $B_0$) and RF coil 7 emits the RF excitation field (i.e., field $B_1$).

Gradient coils 6 produce magnetic field gradients $G_x$, $G_y$, and $G_z$ which are used for position-encoding NMR signals as described above. Gradient coils 6 may consist of three windings, for example, each of which is supplied with current by an amplifier 8a-8c in order to generate a linear gradient field in its respective Cartesian direction (i.e., x, y, or z). Each amplifier 8a-8c includes a digital-analog converter 9a-9c which is controlled by a sequence controller 10 to generate desired gradient pulses such that the net gradient-induced phasing over a $T_R$ interval is substantially zero.

Sequence controller 10 also controls the generation of RF pulses by RF system 11. RF system 11 is responsive to a scan prescription and direction from sequence controller 10 to produce RF pulses of the desired timing frequency, phase, and pulse amplitude waveform. The generated RF pulses may be applied to the whole of RF coil 7 or to one or more local coils or coil arrays. RF coil 7 converts the RF pulses emitted by RF amplifier 12, via multiplexer 13, into a magnetic alternating field in order to excite the nuclei and align the nuclear spins of the object to be examined or the region of the object to be examined.

The RF pulses to be produced by RF system 11 are represented digitally as complex numbers. Sequence controller 10 supplies these numbers in real and imaginary parts to digital-analog converters 14a-14b in RF system 11 to create corresponding analog pulse sequences. Transmission channel 15 modulates the pulse sequences with a radio-frequency carrier signal having a base frequency corresponding to the resonance frequency of the nuclear spins in the volume to be imaged.

RF coil 7 both emits the radio-frequency pulse to excite nuclear spins and scans the alternating field which is produced as a result of the precessing nuclear spins, i.e., the nuclear spin echo signals. The received signals are received by multiplexer 13, amplified by RF amplifier 16 and demodulated in receiving channel 17 of RF system 11 in a phase-sensitive manner. Analog-digital converters 18a and 18b convert the demodulated signals into a real part and an imaginary part.

Computing system 20 receives the real and imaginary parts and reconstructs an image therefrom according to known techniques. System 20 may comprise any general-purpose or dedicated computing system. Accordingly, system 20 includes one or more processing units 21 (e.g., processors, processor cores, execution threads, etc.) configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of control program 23. One or more processing units 21 may execute control program 23 to cause system 20 to perform any one or more of the processes described herein. For example, one or more processing units 21 may execute control program 23 to cause system 20 to receive the real and imaginary parts of a received RF signal via MR system interface 24 and reconstruct an image therefrom according to known techniques. Such an image may be stored among acquired images 26 of storage device 22. Control program 23 may also be executed to process one or more reconstructed images as described herein, and to store a processed image among processed images 27 of storage device 22.

One or more processing units 21 may also execute control program 23 to provide instructions to sequence controller 10 via MR system interface 24. For example, sequence controller 10 may be instructed to initiate the desired pulse sequences and corresponding scanning of k-space. In particular, sequence controller 10 may be instructed to control the switching of magnetic field gradients via amplifiers 8a-8c, the transmission of radio-frequency pulses having a defined phase and amplitude via RF system 11 and RF amplifier 12, and the reception of the resulting magnetic resonance signals according to some embodiments.

Acquired images 26 may comprise MR images reconstructed based on received MR signals as mentioned above and known in the art. Motion-corrected images 27 may comprise images generated by applying motion-correction processing to respective ones of acquired images 26, and composite images 28 may comprise images generated based on two or more acquired images 26 and/or motion-corrected images 27 according to embodiments described herein.

Acquired images 26, motion-corrected images 27 and/or composite images 28 may be provided to terminal 30 via UI interface 25 of system 20. UI interface 25 may also receive input from terminal 30, which may be used to provide commands to control program 23 in order to control sequence controller 10 other elements of system 1. Terminal 30 may simply comprise a display device and an input device coupled to system 20. In some embodiments, terminal 30 is a separate computing device such as, but not limited to, a desktop computer, a laptop computer, a tablet computer, and a smartphone.

Each element of system 1 may include other elements which are necessary for the operation thereof, as well as additional elements for providing functions other than those described herein. Storage device 22 may also store data and other program code for providing additional functionality and/or which are necessary for operation of system 20, such as device drivers, operating system files, etc.

Figure 2:
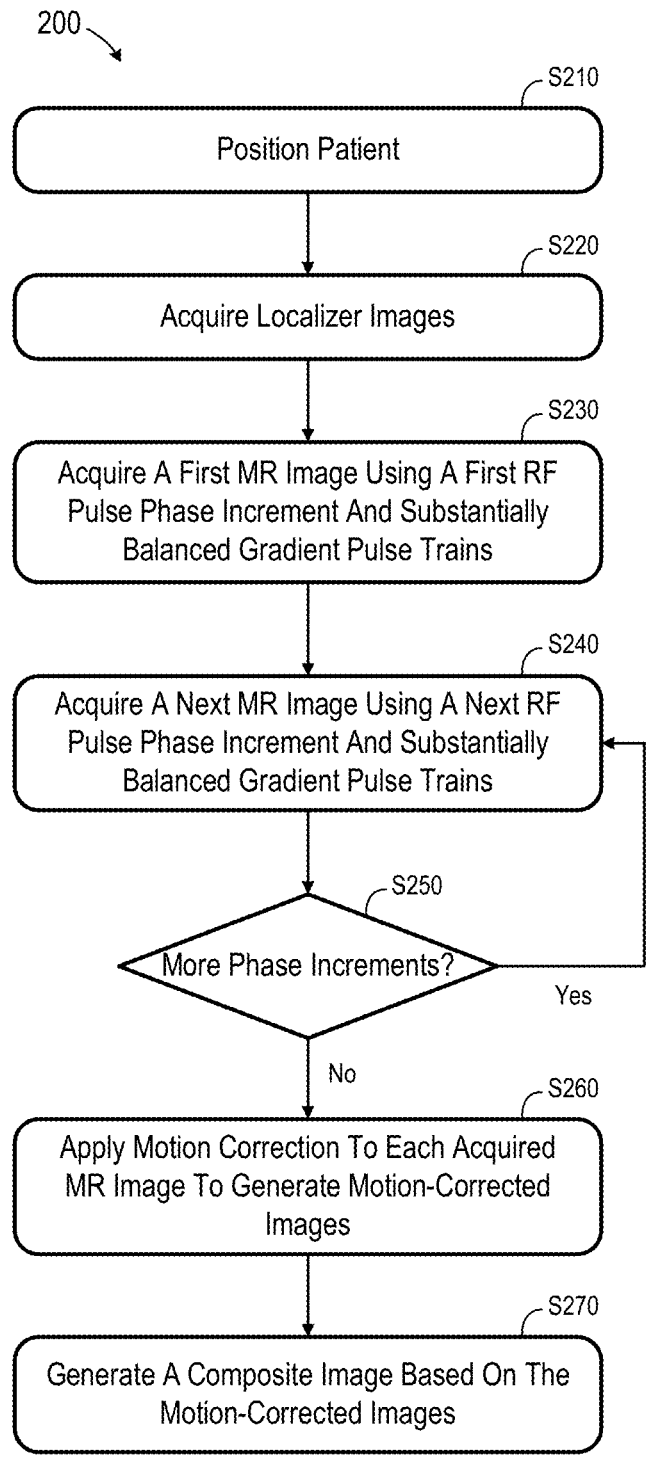
FIG. 2 is a flow diagram of a process according to some embodiments.

FIG. 2 is a flowchart of process 200 according to some embodiments. As will be described, some embodiments of process 200 provide phase-cycled, steady-state, free precession MR imaging.

In some embodiments, various hardware elements of system 1 (e.g., one or more processors) execute program code to perform process 200. Process 200 and all other processes mentioned herein may be embodied in processor-executable program code read from one or more of non-transitory computer-readable media, such as a floppy disk, a disk-based or solid-state hard drive, CD-ROM, a DVD-ROM, a Flash drive, and a magnetic tape, and then stored in a compressed, uncompiled and/or encrypted format. In some embodiments, hard-wired circuitry may be used in place of, or in combination with, program code for implementation of processes according to some embodiments. Embodiments are therefore not limited to any specific combination of hardware and software.

Initially, at S210, a patient is positioned for imaging within an MR imaging device. For example, FIG. 1 illustrates patient 4 positioned within bore 3 of MR imaging chassis 2. Positioning of the patient may be performed using known techniques, and the patient position may be dependent upon the volume of the patient to be imaged. According to some embodiments, receiver RF coils are arranged around the volume of interest.

Next, localizer images are acquired at S220 according to known protocols. The localizer images are acquired using the NMR phenomenon as described above. The localizer images comprise a set of three-plane, low-resolution, large field-of view images. These localizer images are used for plotting positions of the image slices to be acquired.

In this regard, a first MR image is acquired at S230. The image is acquired using an imaging sequence including a first RF pulse phase increment and balanced gradient pulse trains. The sequence of gradient pulses and RF pulses required for each image acquisition described herein may be controlled by sequence controller 10 under command of device 20.

A phase pulse increment is equal to the difference between phases of consecutive RF pulses. The balanced gradient pulse trains preserve longitudinal and transverse magnetization within each RF pulse repetition time interval as is known with respect to conventional steady-state free precession sequences. Since theoretically perfect operation of any MR imaging system is unlikely, it should be understood that the term "balanced" as used herein is meant to encompass substantially-preserved longitudinal and transverse magnetization, in which the net gradient-induced phasing over a $T_R$ interval is substantially zero.

Figure 3A:
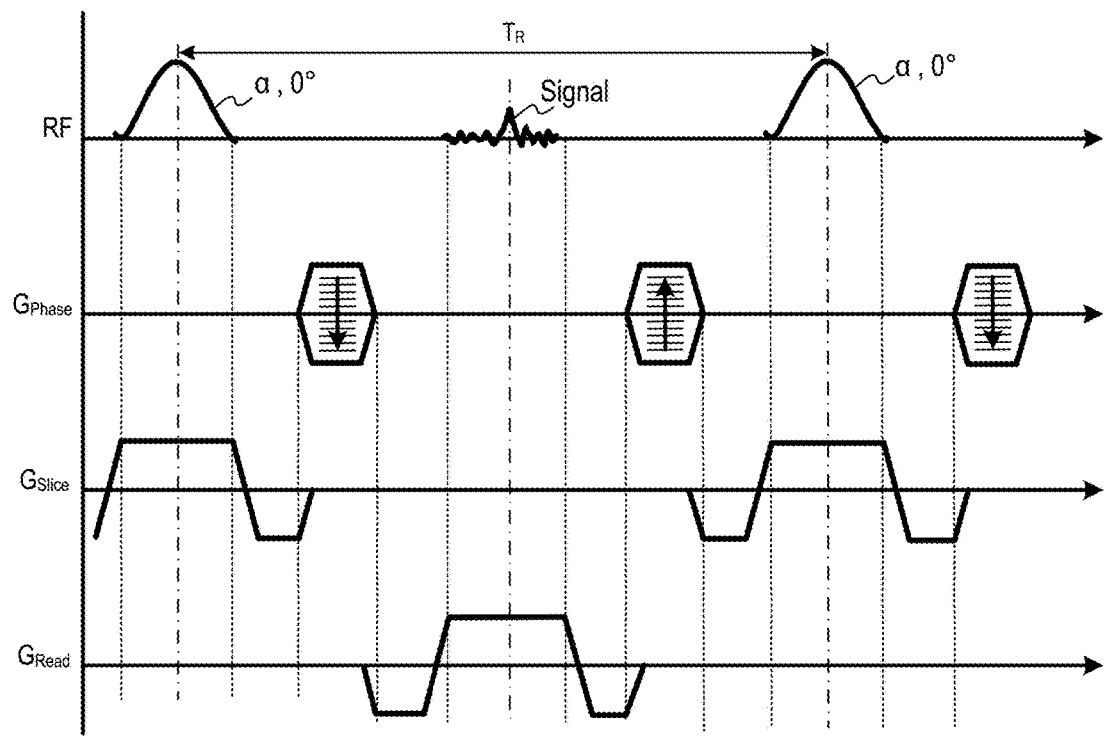
FIG. 3A illustrates an MR sequence using a first phase-cycling scheme according to some embodiments.

FIG. 3A illustrates an imaging sequence according to some embodiments. The gradient pulses $G_{Phase}$, $G_{Slice}$ and $G_{Read}$ are arranged to refocus the free induction decay and echo components of the steady-state free precession signal Signal at the center of the $T_R$ interval, as is known in the art.

The first RF pulse of FIG. 3A is associated with a flip angle α and a phase of 0°. Embodiments are not limited to a 0° phase.

According to some embodiments, the first MR image is acquired using a first RF pulse phase increment of 0°. Accordingly, the next RF pulse of FIG. 3A is associated with a flip angle α and a phase of 0°. The phase is unchanged because the predetermined phase increment is 0°. FIG. 3A illustrates reading of one steady-state free precession signal Signal, and the pattern shown in FIG. 3A repeats to read 60-70 additional signals according to some embodiments. Due to the phase increment of 0°, each RF pulse of the repeated pattern exhibits a same phase (i.e., 0° in the present example).

Figure 3B:
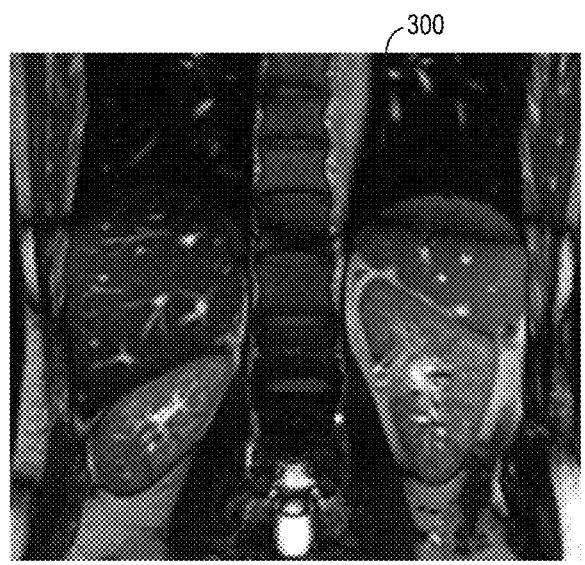
FIG. 3B is an example of an MR image acquired using the MR sequence of FIG. 3A according to some embodiments.

According to an example, the image is acquired at S230 using a 3T scanner and the following imaging parameters: $T_R/T_E$=5.0/2.5 msec, α=80°, field of view=340×340 mm$^2$ with 50% phase oversampling. FIG. 3B illustrates a first MR image 300 acquired at S230 according to some embodiments. Image 300 exhibits high spatial resolution and imaging contrast, but also includes banding artifacts arising from off-resonance effects of the local magnetic field.

Figure 4A:
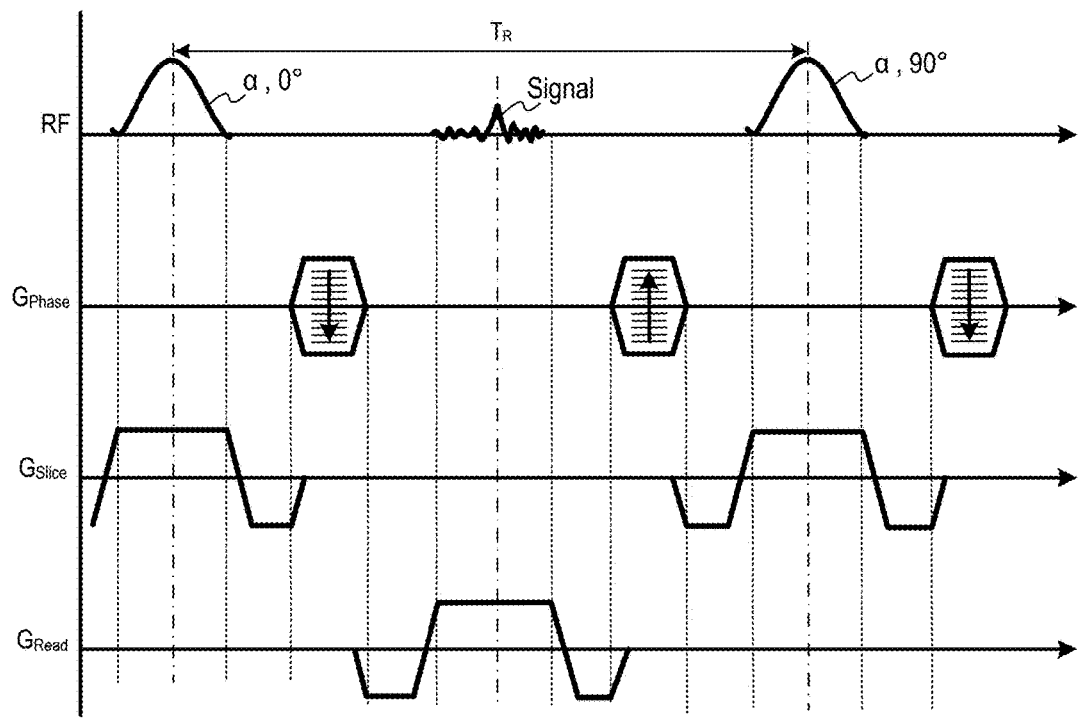
FIG. 4A illustrates an MR sequence using a second phase-cycling scheme according to some embodiments.

A next MR image is acquired at S240. The next image is acquired using balanced gradient pulse trains and a second RF pulse phase increment, for example using the same imaging parameters as set forth above. FIG. 4A illustrates an imaging sequence according to some embodiments of S240. It will be assumed that the second RF pulse phase increment is 90°, but embodiments are not limited thereto.

The sequence of FIG. 4A is identical to the sequence of FIG. 3A (although embodiments are not limited thereto), except that the second RF pulse of FIG. 4A is associated with a flip angle α and a phase of 90° (i.e., 90° greater than the prior RF pulse). Accordingly, the next four pulses in the sequence have phases, respectively, of 180°, 270°, 360°, and 450° (i.e., 90°) and the pattern continues until 60-70 additional signals are read in order to acquire the next image. Techniques for changing the phase of successive RF pulses based on a single pulse phase increment are known and are therefore not described herein.

Figure 4B:
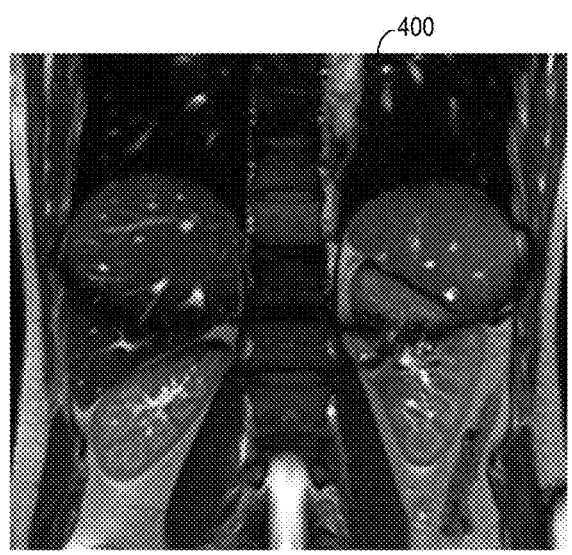
FIG. 4B is an example of an MR image acquired using the MR sequence of FIG. 4A according to some embodiments.

Image 400 of FIG. 4B is acquired at S240 according to the present example. Like image 300, image 400 exhibits banding artifacts arising from off-resonance effects.

At S250, it is determined whether another image should be acquired using another pulse phase increment. The number of pulse phase increments and the values of each pulse phase increment may be established by an operator, by software settings or otherwise determined prior to execution of process 300. For example, embodiments may utilize any number of phase increments and any particular phase increments.

Figure 5A:
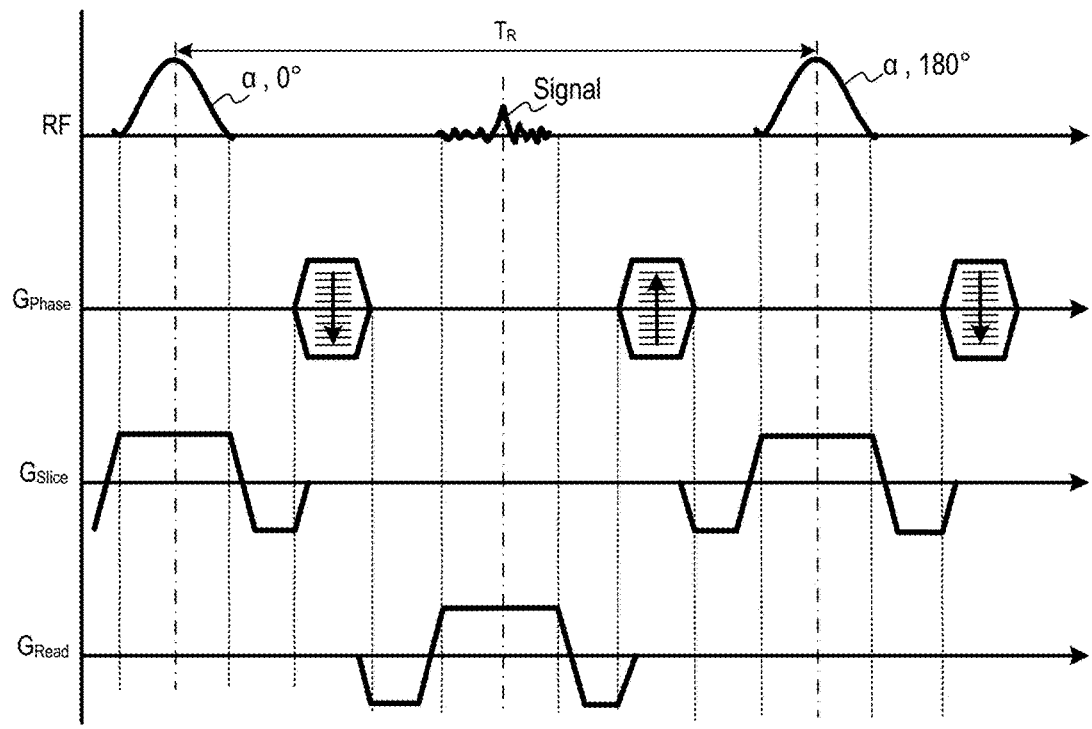
FIG. 5A illustrates an MR sequence using a third phase-cycling scheme according to some embodiments.

The present example utilizes four phase increments: 0°; 90°; 180°; and 270°. Accordingly, flow returns to S240 to acquire a next MR image using a 180° pulse phase increment and substantially-balanced gradient pulse trains. FIG. 5A illustrates such an imaging sequence, in which the first RF pulse is associated with a flip angle α and a phase of 0° and the second RF pulse is associated with a flip angle α and a phase of 180°. In view of the 180° pulse phase increment, the next four pulses in the sequence have phases, respectively, of 360°, 540°, 720°, and 900°.

Figure 5B:
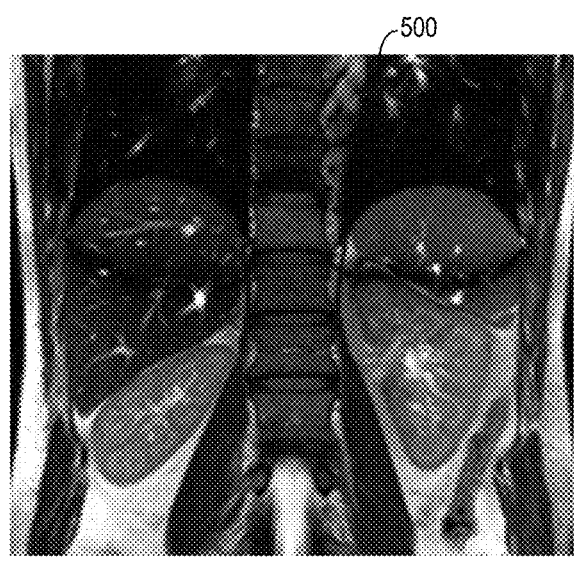
FIG. 5B is an example of an MR image acquired using the MR sequence of FIG. 5A according to some embodiments.

As described above, the pattern continues until 60-70 additional signals are read in order to acquire the next image. Image 500 of FIG. 5B, exhibits banding artifacts, may be acquired at S240 according to the present example.

Figure 6A:
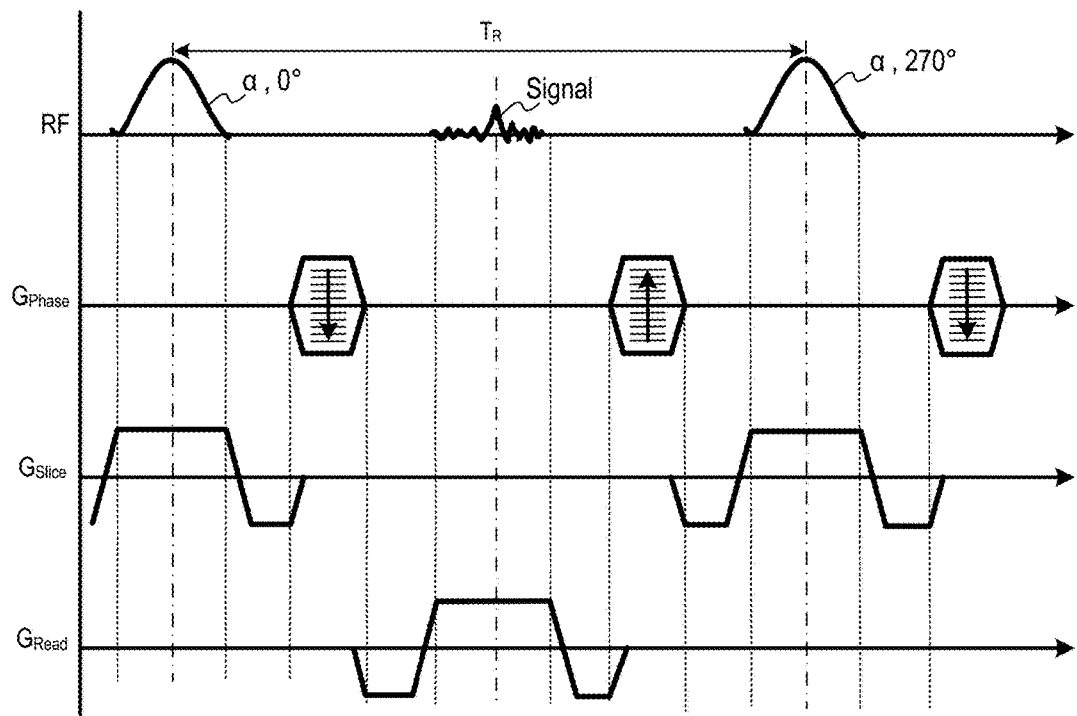
FIG. 6A illustrates an MR sequence using a fourth phase-cycling scheme according to some embodiments.
Figure 6B:
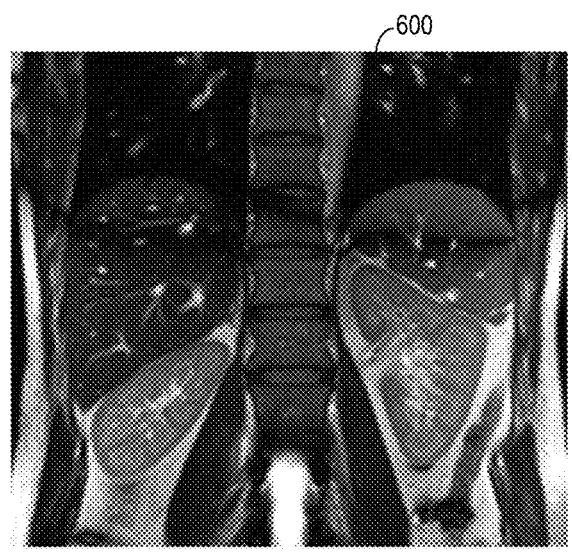
FIG. 6B is an example of an MR image acquired using the MR sequence of FIG. 6A according to some embodiments.

Continuing the present example, it is again determined at S250 that another image should be acquired using a 270° pulse phase increment. Flow returns to S240 to acquire a next MR image using a 270° pulse phase increment, for example using the imaging sequence of FIG. 6A. As shown, the first RF pulse is associated with a flip angle α and a phase of 0° and the second RF pulse is associated with a flip angle α and a phase of 270°. The next four RF pulses in the 270° phase-cycled sequence have phases, respectively, of 540°, 810°, 1080°, and 1350°. FIG. 6B illustrates image 600 acquired at S240 according to the present example.

Flow proceeds from S250 to S260 after determining that an image has been acquired for each desired pulse phase increment. Motion correction is applied to each acquired image at S260 to generate corresponding motion-corrected images. S260 may utilize any motion correction processing algorithm that is or becomes known. In one example, non-rigid motion correction is applied to correct for elastic motion of soft tissues. Examples of non-rigid motion correction are described in Xue et al., "Phase-sensitive inversion recovery for myocardial T1 mapping with motion correction and parametric fitting", Magn. Reson. Med. 2013; 69(5):1408-20, and Kellman et al., "High spatial and temporal resolution cardiac cine MRI from retrospective reconstruction of data acquired in real time using motion correction and resorting", Magn. Reson. Med. 2009;62(6): 1557-64.

Next, at S270, a composite image is generated based on the motion-corrected images. Returning to the present example, a single image may be generated at S270 from four motion-corrected images generated at S260. These four motion-corrected images were in turn generated based on the four MR images acquired using respective phase-cycling schemes.

According to some embodiments, generation of the composite image at S270 comprises directly averaging the motion-corrected images. Specifically, the value of each pixel in the composite image is equal to the average of the values of the same pixel in each of the motion-corrected images. Regardless of this example, generation of the composite image may involve any degree of computational complexity, including but not limited to image-region- or pixel-specific weighted averaging.

Figure 7A:
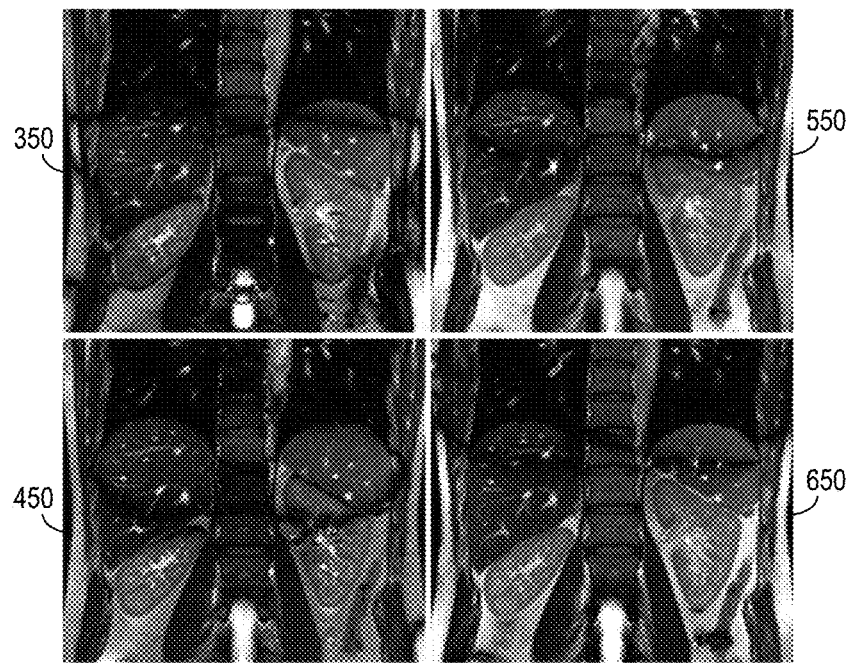
FIG. 7A illustrates examples motion-corrected MR images corresponding to respective ones of the MR images of FIGS. 3B, 4B, 5B and 6B according to some embodiments.
Figure 7B:
FIG. 7B illustrates a composite MR image generated based on the MR images of FIG. 7A according to some embodiments.

FIG. 7A illustrates motion-corrected versions 350, 450, 550 and 650 of each of images 300, 400, 500 and 600, and FIG. 7B illustrates composite image 700 generated at S270 according to some embodiments. The pixels of image 700 reflect averages of corresponding pixels of motion-corrected images 350, 450, 550 and 650. The banding artifacts have been removed without compromising clarity.

Embodiments may therefore address banding artifacts at high magnetic field strengths without requiring short $T_R$ and low flip angle. Consequently, these parameters and others may be fully utilized to optimize signal intensity of targeted tissue and the imaging contrast between soft tissues.

Some embodiments provide multi-slice image acquisition at S230 and S240. Such embodiments also utilize balanced gradients and phase-incremented RF pulses as described above, but, as is known in the art, the gradients coupled to each RF pulse vary per acquired slice. According to such embodiments, the images acquired at S230 and S240 are three-dimensional images, and the images generated at S260 and S270 are also three-dimensional images.

The foregoing diagrams represent logical architectures for describing processes according to some embodiments, and actual implementations may include more or different components arranged in other manners. Other topologies may be used in conjunction with other embodiments. Moreover, each component or device described herein may be implemented by any number of devices in communication via any number of other public and/or private networks. Two or more of such computing devices may be located remote from one another and may communicate with one another via any known manner of network(s) and/or a dedicated connection. Each component or device may comprise any number of hardware and/or software elements suitable to provide the functions described herein as well as any other functions. For example, any computing device used in an implementation of a system according to some embodiments may include a processor to execute program code such that the computing device operates as described herein.

Embodiments described herein are solely for the purpose of illustration. Those in the art will recognize other embodiments may be practiced with modifications and alterations to that described above.

What is claimed is:

1. A system comprising:
a chassis defining a bore;
a main magnet to generate a polarizing magnetic field within the bore;
a gradient system to apply a gradient magnetic field to the polarizing magnetic field;
a radio frequency (RF) system to apply an RF pulse to patient tissue disposed within the bore and to receive signals from the patient tissue; and
a computing system to receive the signals from the RF system, the computing system to execute program code to:
control the gradient system and the radio frequency system to generate a first imaging sequence comprising first balanced gradient pulse trains and RF pulses, where phases of successive RF pulses in the first imaging sequence differ by a first pulse phase increment, to detect first signals emitted from the patient tissue in response to the first imaging sequence, and to generate a first image based on the first signals;
control the gradient system and the radio frequency system to generate a second imaging sequence comprising second balanced gradient pulse trains and RF pulses, where phases of successive RF pulses in the second imaging sequence differ by a second pulse phase increment different from the first pulse phase increment, to detect second signals emitted from the patient tissue in response to the second imaging sequence, and to generate a second image based on the second signals;
control the gradient system and the radio frequency system to generate a third imaging sequence comprising third balanced gradient pulse trains and RF pulses, where phases of successive RF pulses in the third imaging sequence differ by a third pulse phase increment different from the first pulse phase increment and the second pulse phase increment, to detect third signals emitted from the patient tissue in response to the third imaging sequence, and to generate a third image based on the third signals;
apply motion-correction processing to the first image to generate a first motion-corrected image;
apply motion-correction processing to the second image to generate a second motion-corrected image;
apply motion-correction processing to the third image to generate a third motion-corrected image; and
generate a composite image based on the first motion-corrected image, the second motion-corrected image and the third motion-corrected image.

2. A system according to claim 1,
wherein generation of the composite image comprises averaging the first motion-corrected image, the second motion-corrected image, and the third motion-corrected image.

3. A system according to claim 1,
wherein generation of the composite image comprises averaging the first image, second image and the third image.

4. A system according to claim 1,
wherein each of the first image, the second image, the third image and the composite image is a three-dimensional image.

5. A method comprising:
applying, to patient tissue, a first imaging sequence comprising first balanced gradient pulse trains and radio frequency (RF) pulses, where phases of successive RF pulses in the first imaging sequence differ by a first pulse phase increment;
detecting first signals emitted from the patient tissue in response to the first imaging sequence, and to generate a first image based on the first signals;
applying, to the patient tissue, a second imaging sequence comprising second balanced gradient pulse trains and RF pulses, where phases of successive RF pulses in the second imaging sequence differ by a second pulse phase increment different from the first pulse phase increment;
detecting second signals emitted from the patient tissue in response to the second imaging sequence, and to generate a second image based on the second signals;
applying, to the patient tissue, a third imaging sequence comprising third balanced gradient pulse trains and RF pulses, where phases of successive RF pulses in the third imaging sequence differ by a third pulse phase increment different from the first pulse phase increment and the second pulse phase increment;
detecting third signals emitted from the patient tissue in response to the third imaging sequence, and to generate a third image based on the third signals;
applying motion-correction processing to the first image to generate a first motion-corrected image;
applying motion-correction processing to the second image to generate a second motion-corrected image;
applying motion-correction processing to the third image to generate a third motion-corrected image;
generating a composite image based on the first motion-corrected image, the second motion-corrected image and the third motion-corrected image; and
displaying the composite image of the patient tissue on a user interface.

6. A method according to claim 5,
wherein generating the composite image comprises averaging the first motion-corrected image, the second motion-corrected image, and the third motion-corrected image.

7. A method according to claim 5,
wherein generating the composite image comprises averaging the first image, the second image and the third image.

8. A method according to claim 5,
wherein each of the first image, the second image, the third image and the composite image is a three-dimensional image.

9. A method comprising:
acquiring a first image of a patient tissue using a first steady-state free precession magnetic resonance imaging sequence, where successive radio frequency (RF) pulses of the first imaging sequence differ by a first pulse phase increment;

acquiring a second image of the patient tissue using a second steady-state free precession magnetic resonance imaging sequence, where successive RF pulses of the first imaging sequence differ by a second pulse phase increment different from the first pulse phase increment;

acquiring a third image of the patient tissue using a third steady-state free precession magnetic resonance imaging sequence, where successive RF pulses of the third imaging sequence differ by a third pulse phase increment different from the first pulse phase increment and the second pulse phase increment;

applying motion-correction processing to the first image to generate a first motion-corrected image;

applying motion-correction processing to the second image to generate a second motion-corrected image; and applying motion-correction processing to the third image to generate a third motion-corrected image;

generating a composite image based on the first motion-corrected image, the second motion-corrected image, and the third motion-corrected image; and displaying the composite image of the patient tissue on a user interface.

10. A method according to claim 9,
wherein generating the composite image comprises averaging the first motion-corrected image, the second motion-corrected image, and the third motion-corrected image.

11. A method according to claim 9,
wherein generating the composite image comprises averaging the first image, the second image and the third image.

12. A method according to claim 9,
wherein each of the first image, the second image, the third image and the composite image is a three-dimensional image.

* * * * *